(12) United States Patent
Kyle et al.

(10) Patent No.: US 8,587,437 B2
(45) Date of Patent: Nov. 19, 2013

(54) WIRELESS HAND HYGIENE MONITORING SYSTEM

(75) Inventors: James Robert Kyle, Whitby (CA); Jeffery Donald Brink, Oshawa (CA); Leigh Francis McIsaac, Toronto (CA)

(73) Assignee: The Stable Group Incorporated, Markham (CA)

( * ) Notice: Subject to any disclaimer, the term of this patent is extended or adjusted under 35 U.S.C. 154(b) by 507 days.

(21) Appl. No.: 12/822,301

(22) Filed: Jun. 24, 2010

(65) Prior Publication Data

US 2010/0328076 A1    Dec. 30, 2010

Related U.S. Application Data

(60) Provisional application No. 61/219,941, filed on Jun. 24, 2009.

(51) Int. Cl.
*G08B 23/00* (2006.01)

(52) U.S. Cl.
USPC ........................................ 340/573.1

(58) Field of Classification Search
USPC ............... 340/573.1, 529, 539.11, 539.21, 340/539.23, 13.24
See application file for complete search history.

(56) References Cited

U.S. PATENT DOCUMENTS

| | | | |
|---|---|---|---|
| 5,202,666 A | 4/1993 | Knippscheer | |
| 5,945,910 A | 8/1999 | Gorra | |
| 6,125,482 A | 10/2000 | Foster | |
| 6,236,317 B1 | 5/2001 | Gohen | |
| 6,392,546 B1 | 5/2002 | Smith | |
| 6,426,701 B1 | 7/2002 | Levy | |
| 6,975,231 B2 | 12/2005 | Lane | |
| 7,271,728 B2 | 9/2007 | Taylor | |
| 7,372,367 B2 | 5/2008 | Lane | |
| 7,375,640 B1 | 5/2008 | Plost | |
| 7,605,704 B2 * | 10/2009 | Munro et al. | 340/572.1 |
| 7,659,824 B2 * | 2/2010 | Prodanovich et al. | 340/573.1 |
| 7,682,464 B2 | 3/2010 | Glenn | |
| 7,755,494 B2 | 7/2010 | Melker | |
| 7,812,730 B2 * | 10/2010 | Wildman et al. | 340/573.1 |
| 7,893,842 B2 * | 2/2011 | Deutsch | 340/573.1 |
| 7,978,083 B2 * | 7/2011 | Melker et al. | 340/573.1 |
| 8,212,653 B1 * | 7/2012 | Goldstein et al. | 340/10.1 |
| 2007/0020212 A1 | 1/2007 | Bernal | |
| 2007/0229288 A1 | 10/2007 | Ogrin | |
| 2008/0001763 A1 * | 1/2008 | Raja et al. | 340/573.1 |
| 2008/0087719 A1 | 4/2008 | Sahud | |
| 2008/0246599 A1 * | 10/2008 | Hufton et al. | 340/529 |
| 2009/0031020 A1 * | 1/2009 | Garcia et al. | 709/224 |
| 2009/0084407 A1 | 4/2009 | Glenn | |

* cited by examiner

*Primary Examiner* — Phung Nguyen

(74) *Attorney, Agent, or Firm* — Marshall & Melhorn, LLC

(57) ABSTRACT

A method and mobile electronic device for monitoring hand hygiene policy compliance is provided. The device comprises a radio transceiver and is configured to detect proximity to base stations by measuring radio signal strength from the base stations and to communicate the proximity information to a central computer via the radio transceiver and to receive notification of compliance or non-compliance with the hand hygiene policy from the central computer. The central computer determines compliance by tracking the location of device in relation to the base stations and monitoring hand hygiene events reported by hand hygiene base stations.

4 Claims, 3 Drawing Sheets

WIRELESS HAND HYGIENE MONITORING SYSTEM

This application claims the benefit of and priority to U.S. Provisional Patent Application No. 61/219,941 filed Jun. 24, 2009, the contents of which are incorporated herein by reference.

TECHNICAL FIELD

This disclosure relates to the field of systems for monitoring hand hygiene.

BACKGROUND

Hospitals and other health care facilities have long struggled with hand hygiene as one of the most important tools in fighting the spread of infection. With the outbreak of SARS in 2003 and the H1N1 flu outbreak in Mexico in 2009, there has been an increased awareness of hand hygiene around the world, not just in health care, food processing, and other environments involving high risk of infection, but also in environments where hand hygiene has not traditionally been emphasized as a public health and safety issue.

Where a hand hygiene policy has been formulated for employees or other users of a facility, it must be communicated and enforced. Monitoring compliance with the policy allows administrators to target their communication and enforcement efforts and reduce costs associated with non-compliance.

SUMMARY

According to one example embodiment is a method for monitoring hand hygiene policy in a communication system that includes at least one mobile electronic device having a radio transceiver, at least one wireless base station and a central computer. The method includes detecting through the radio transceiver of the mobile electronic device at least one signal of at least one radio transmitter of at least one base station; communicating signal strength data indicating the strength of the at least one signal from the mobile electronic device to the central computer by means of the radio transceiver; and determining at the central computer whether a user of the mobile electronic device is in compliance with a hand hygiene policy based at least partially on the signal strength data received from the mobile electronic device.

According to another example embodiment, there is provided a method for monitoring hand hygiene policy compliance for a system that includes a plurality of mobile electronic devices each associated with a device user, a plurality of hand hygiene stations at which device users can perform hand hygiene events and that are each enabled to transmit wireless signals, and a central computer enabled to exchange messages with the mobile electronic devices using a wireless network. The method includes: receiving at the central computer messages from the wireless network sent by at least some of the mobile electronic devices, at least some of the messages including proximity information representing the proximity of the sending mobile electronic devices to one or more of the hand hygiene stations; and determining at the central computer whether the mobile electronic device users are in compliance with the hand hygiene policy at least partially in dependence on the proximity information.

According to another example embodiment is an automated system for monitoring compliance with a hand hygiene policy at a facility having a wireless local area network (WLAN). The system includes: a compliance computer in communication with the WLAN; a plurality of hand hygiene stations at the facility, each of the hand hygiene stations being associated with a location where a hand hygiene event can be performed and enabled to communicate with the WLAN; and a plurality of mobile electronic devices enabled to communicate with the WLAN, each being associated with a device user and being configured to periodically measure received signal strengths of signals received from the hand hygiene stations and send messages to the compliance computer through the WLAN that includes proximity information representing the measured received signal strengths and identifying the hand hygiene stations from which the signals were received. The compliance computer is configured to determine whether the mobile electronic device users are in compliance with the hand hygiene policy at least partially in dependence on the proximity information.

According to another example embodiment a mobile electronic device for monitoring hand hygiene policy compliance is provided. The device comprises a radio transceiver and is configured to detect proximity to base stations by measuring radio signal strength from the base stations and to communicate the proximity information to a central computer via the radio transceiver and to receive notification of compliance or non-compliance with the hand hygiene policy from the central computer. The central computer determines compliance by tracking the location of device in relation to the base stations and monitoring hand hygiene events reported by hand hygiene base stations.

DETAILED DESCRIPTION OF EXAMPLE EMBODIMENTS

Figure 1:
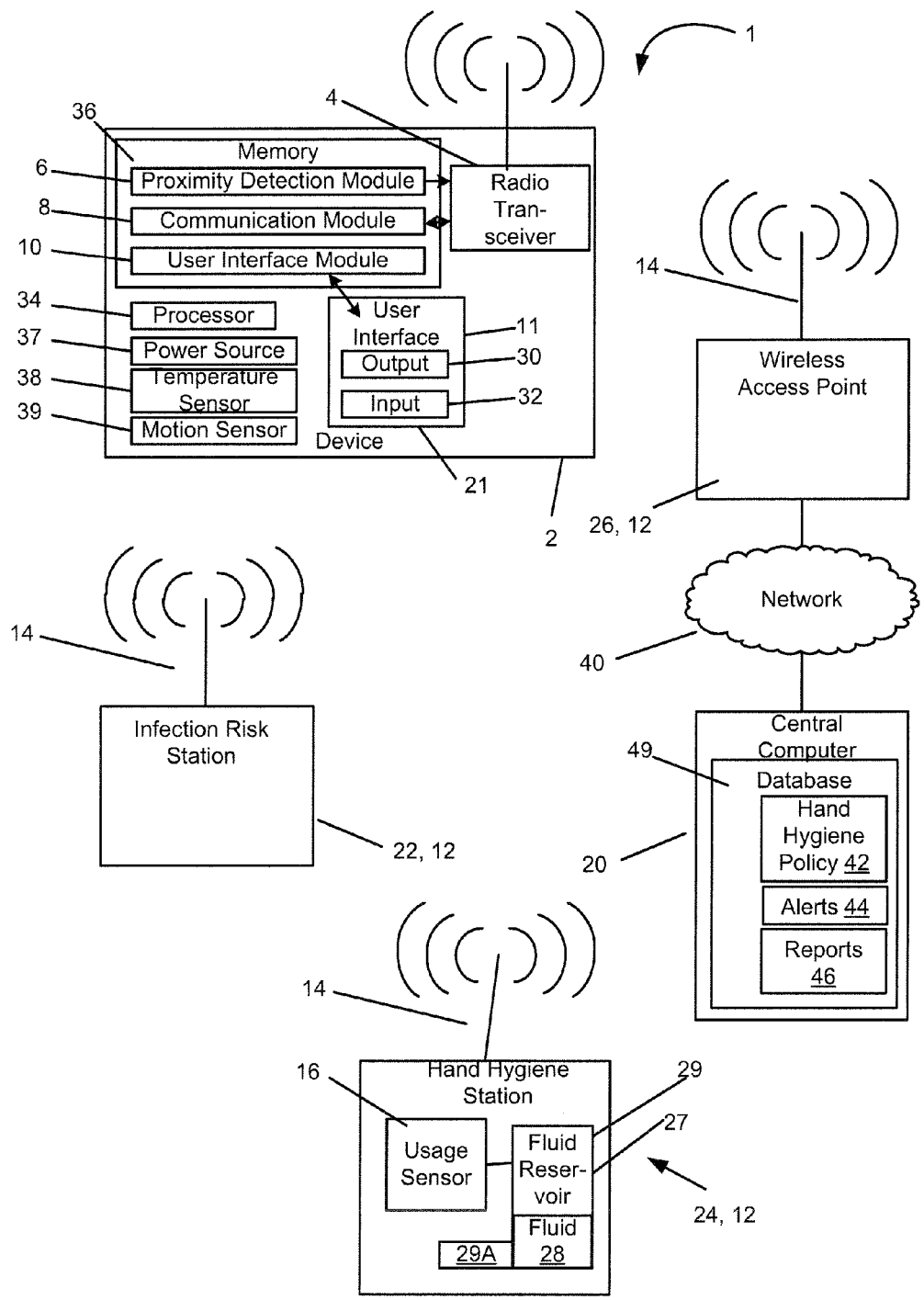
FIG. 1 is a block diagram of one embodiment of the system and device, showing all components operating together.

With reference to FIG. 1, a system 1 for monitoring hand hygiene policy compliance is shown in accordance with example embodiments. The hand washing policy compliance and monitoring system 1 includes a mobile electronic device 2 that is associated with an individual, one or more base stations 12, and a central computer 20. As will be explained in greater detail below, base stations 12 can take different forms, including for example hand hygiene stations 16, infection risk stations 22 and wireless access points 26. In one example embodiment, the hand hygiene policy compliance and monitoring system 1 operates by tracking the location of the device 2, carried by a user, within an environment containing base stations 12 such as hand hygiene stations 24 and infection risk stations 22 (which may for example identify locations of higher risk for receiving or transmitting infection such as patient beds in a hospital or food handling stations in a food processing environment). The mobile electronic device 2 location is tracked by using a radio transceiver 4 on the device 2 to measure the strength of radio signals produced by base stations 12 in the environment and relaying this information to the central computer 20. The central computer 20 uses the known locations of the base stations 12 to determine the location of the device 2, and uses this location information to determine when the user carrying the device 2 is in proximity to hand hygiene stations 24 and to infection risk stations 22, for how long, and in what sequence. Using this location information, possibly supplemented with other information gathered from the base stations 12 themselves, the central computer 20 determines whether the user carrying the device 2 is in compliance with a hand hygiene policy 42. This determination can then be made the basis for generating reports 46 and alerts 44 for the user or for an administrator of the policy 42 for the purpose of enforcement, education, research, or other administrative goals.

The device 2 may take any of a number of forms, and more than one type of device may be used in parallel in the system 1. The device 2 may by way of non limiting example be a 802.11-enabled cell phone, 802.11-enabled personal digital assistant (PDA), 802.11 pager, VoIP phone, electronic badge in the form of a credit card style tag worn on a lanyard around the neck or clipped to the wearers clothing for example, or any other device carried by a user and having a radio transceiver 4 capable of detecting nearby base stations 12 and communicating the relevant information to the central computer 20. The following description will, in at least some embodiments, describe the operation of the system 1 using a 'smart phone' (cell phone with PDA capabilities) to implement mobile electronic device 2, but it will be understood that most or all of the features of the device 2 and system 1 can be carried out using any of the device types mentioned above. One or more types of device may operate on the system 1 at any given time, and different types of device may be issued to different types of users (e.g. administrators may be issued full-feature smart phones, staff may be issued pagers, and temporary visitors to the facility may be issued electronic badges).

The base stations 12 used by the system 1 can be any fixed or mobile location having a radio transmitter 14. Although base stations implemented as hand hygiene stations 24 and infection risk stations 22 are described herein in detail, other locations or articles in the environment being monitored may be equipped with radio transmitters 14 as well, allowing the system 1 to monitor additional activities of the user or additional environmental factors affecting hand hygiene policy compliance.

As noted above, one type of base station 12 is a hand hygiene station 24. A hand hygiene station 24 serves in a location where a user can perform a hand hygiene operation or event such as clean his or her hands in accordance with a hand hygiene policy 42. It may be embodied as a basin and sink, possibly having a dispenser for hand washing soap or solution. It may alternatively be embodied as a hand hygiene fluid dispenser 27 which can dispense a fluid 28 such as a liquid or foam sanitizer from a reservoir 29. The hand hygiene station 24 has a radio transmitter 14, which is used by the device 2 to determine its location relative to the station. The station may also be equipped with a usage sensor 16 for determining when a person is using it for hand washing. This sensor 16 may comprise a motion sensor for detecting a user's hands placed under a faucet, in a basin, or under a fluid dispenser 27. The usage sensor 16 may alternatively comprise a mechanical and/or motion sensor for detecting depression of a lever for dispensing fluid 28 from a reservoir 29, or a waterwheel or other sensor for detecting water flow through a faucet. Data from the usage sensor 16 is relayed from the hand hygiene station 24 to the central computer 20 using the radio transmitter 14, which may by way of non limiting example a transceiver implemented using an IEEE 802.11 compliant device such as an 802.11a/b/g or n device. For example data from sensor 16 could be transmitted to central computer 20 directly through a wireless access point 26, or indirectly relayed through a nearby mobile electronic device 2.

As noted above, a second type of base station 12 is an infection risk station 22. Such stations may be located for example at a patient bed in a hospital, a food handling station in a food processing environment, or any other location where a user is likely to either come into contact with contaminants or to communicate contaminants from his or her hands to someone or something present at the station 22. In some embodiments, an infection risk station 22 may be combined with a hand hygiene station 24, allowing a user to wash his or her hands before and/or after handling the infection risk. Like the example hand hygiene station 24, the infection risk station 22 has a radio transmitter 14 used to signal its location to the device 2. The radio transmitter 14 may additionally communicate information to the central computer 20.

As noted above, a third type of base station 12 is a wireless access point 26. This type of base station 12 has a radio transceiver such as transceiver 14 used to relay communications between the device 2 or another base station 12 and the central computer 20. The wireless access point 26 is in communication with the central computer 20 through a network 40 such as an Ethernet network or some other communication means, including a wireless network. When reporting the signal strength of nearby base stations 12 to the central computer 20, the device 2 may include the signal strength of nearby wireless access points 26.

The device 2 uses a radio transceiver 4 to communicate with the central computer 20 and to detect the radio signals produced by nearby base stations 12. In one example embodiment, this radio transceiver 4 comprises an 802.11 radio apparatus (for example 802.11a/b/g or n apparatus) with associated logic required to communicate over the radio apparatus. The signal strength of a base station 12 using the 802.11 protocol is typically measured as received signal strength indication (RSSI) indicating the dBm of the received signal and represented as a one-byte unsigned integer with values between 0 and 255. These values can be used as a proxy for proximity of the device 2 to base stations 12, although individual stations may exhibit variation in the degree to which RSSI corresponds to proximity. These variations can be accounted for by the central computer 20 by applying different metrics and thresholds to different stations in determining device proximity.

In alternate embodiments of the system 1, the 802.11 components could be replaced by a number of radio or microwave-frequency technologies (e.g., WiMax™, Bluetooth™, GSM, CDMA, 802.15, RFID, W-CDMA) or non-radio technologies (such as some combination of infrared, ultrasonic, magnetic-induction, and/or electrical contact) for the purposes of sensing proximity and/or communication among different elements of the system 1, without materially changing its operation. Embodiments of the system 1 using a wireless network such as an 802.11 network can in some applications offer advantages. By allowing the device 2 and the base stations 12 to communicate with the computer 20 via a wireless network provided by the wireless access points 26, the system 1 can be extended to cover a large area, and it is freed from the constraints of direct electrical connections or line-of-sight data transmission. Thus, in addition to wider coverage, the use of a wireless network affords flexibility and reliability in a dynamic environment where lines may be cut or uncoupled, or lines of sight may be blocked. Furthermore, by using the same medium and apparatus (e.g. 802.11 radio apparatus and protocol) for communication with the central computer 20 and for detecting proximity between devices 2 and base stations 12, the complexity, size, power requirements, and cost of the device 2 and the base stations 12 are minimized. Wireless networks such as 802.11 networks are often a common basis for network communication in large facilities, and the system 1 can be implemented efficiently by exploiting the existing wireless network infrastructure of a facility and using commodity hardware and/or software.

In an example embodiment of the device 2 (including but not limited to a smart phone embodiment), a processor 34 runs software operating the various components of the device 2, including the 802.11 radio transceiver 4. This software is stored in the device's memory 36 and includes software that is executed by processor 34 to implement several modules operating to perform various tasks on the device 2. One module is a proximity detection module 6, which operates to collect RSSI data from nearby base stations 12 via the radio transceiver 4. Another module is the communication module 8, which operates to send RSSI and other data to the central computer 20 over the radio transceiver 4. The device 2 may further include a user interface module 10 operating to detect user input via one or more user input means 32 (such as buttons, a keypad, a keyboard, a scroll wheel, a touch screen, etc.) and to report information to the user via one or more user output means 30 (such as a display screen, loudspeaker, vibratory motor, LED lights, alarm bell, etc.). User input collected via the user interface module 10 may be reported to the central computer 20 along with or in addition to proximity detection data. Other modules may operate via the software running on the device 2 to perform functions unrelated to the compliance system or to otherwise collect, send, receive, or communicate information relevant to the system 1.

The proximity detection module 6 periodically samples the RSSI data for each base station 12 detected by the device 2. In one embodiment, the measurements are taken over a 500 millisecond period, with the minimum, maximum, and average RSSI included in reports to the central computer 20. In one example embodiment, the signals from available base stations 12 are measured every 3 seconds under ordinary conditions. The device 2 may apply a metric to the measured RSSI data whereby only base stations 12 reporting above a predetermined RSSI are included in its data report to the central computer 20. Receiving minimum, average, and maximum RSSI readings from the device 2 allows the computer 20 to weight the RSSI readings from a given station 12 based on the amount of variation shown in the readings, thereby determining whether additional processing is required to pinpoint the device's 2 location. For each base station 12 detected, or each station above the RSSI threshold, the device 2 communicates the RSSI data, along with an identifier identifying the base station 12 (such as a MAC address), to the central computer 20 via a wireless communication channel. This channel may be created between the device 2 and one of the wireless access points 26 through standard UDP or TCP/IP methods. In one embodiment, the devices 2 all have the same IP address and communicate with the central computer 20 using UDP packets, obviating the need for managing IP addresses for the devices 2 or leasing them via DHCP. The computer 20 differentiates packets from different devices 2 based on the originating MAC address. The proximity detection module 6 is also used by the device 2 in some embodiments to select a wireless access point 26 for the communication module 8 to use in reporting data to the central computer 20. The device 2 compares the RSSI readings of all stations in the area that report as wireless access points 26 using the system's SSID, and selects the access point with the strongest RSSI to use for communication with the central computer 20. Accordingly, in an example embodiment, the mobile electronic device 2 periodically measures the signal strength of all the access points or base stations in the wireless local area network that it is operating in and then sends the measurement results to the central computer 20 over the wireless local area network. In embodiments where the device 2 is a tag dedicated for functioning in the hand hygiene compliance system 1, it may be configured to operate in a reduced power state between measurement times (for example, the device 2 could wake up every 3 seconds to measure the radio environment).

The central computer 20 may dynamically configure various parameters used by the device 2 in its proximity detection and communication operations. For example, the device 2 may be configured to periodically query the computer 20 through wireless access point 26 to obtain any update notifications; if the computer 20 responds with updated parameters, the device 2 receives these new parameters and uses them to configure its proximity detection 6 and communication 8 modules. In this manner, the RSSI threshold for reporting a base station 12, the number of base station 12 RSSI measurements to report, the default duration between RSSI reports, and the duration between update queries may be dynamically configured by the central computer 20. Additionally, the network parameters used to communicate with the central computer 20, such as a server's and/or the central computer's IP address, the IP addresses of additional computers used by the system 1, the ports used for communication, the 802.11 SSID, and other network communication parameters may be set according to instructions sent from the central computer 20. These parameters and thresholds may further be stored in the memory 36 of the device 2 for later use. The ability to dynamically update the devices' parameters allows administrators to adapt the system 1 to changing conditions, and to allow new and different device types to be deployed on the system 1 by issuing different parameters to the different device types.

In one embodiment, the central computer 20 comprises a general purpose computer equipped with a network communication interface allowing it to send and receive information to and from the device 2 and the base stations 12, generally by means of a communication network 40 connected to the wireless access points 26 in the environment. The computer 20 runs software allowing it to store and process base station RSSI data from the device 2 and determine, based on known characteristics of the base stations 12, how close the device 2 is to each reported base station 12 at a given time and whether the pattern of device proximity to various base stations 12 indicates compliance with the hand hygiene policy 42. The computer 20 may store information about each base station 12 indicating, among other things: where it is located; what value of RSSI corresponds to what distance from the station; how close a user has to be to the station to trigger a compliance or non-compliance event; and the base station type (e.g. hand hygiene station 24, infection risk station 22, or wireless access point 26). In some embodiments, direct access to the computer 20 itself may be available through a user interface system 21, such as a display screen/keyboard/mouse system, a display screen and buttons, or a remote administration interface (e.g. an HTTP interface accessed through a web browser). An administrator may be able to view reports 46 or alerts 44 tracked by central computer 20, or to alter the operational parameters of the system 1, via such an interface system.

Although a general purpose computer is described as one embodiment of the central computer 20, a skilled person will appreciate that alternative embodiments would perform substantially the same functions. For instance, the computer 20 may comprise a dedicated electronic appliance without general purpose computational capabilities. It may also be embodied as multiple computers or appliances on a communication network 40, each carrying out a subset of the functions of the central computer 20 as described, or each performing the functions of the central computer 20 for a subset of the devices 2 or spatial regions of the environment. In such a multi-computer embodiment, the device 2 may be configured to switch from one computer to another based on instructions received from the computer 20. The device 2 may also be configured to send and receive data to different computers for different purposes, e.g., to send proximity data to a database server, to receive configuration instructions from a configuration server, and to receive alerts 44 and reports 46 from a reporting server.

The device 2 may be configured to report RSSI data to the computer 20 at set periods of time, upon detecting certain events, or both. The device 2 may be configured to spend most of the time in a power-saving mode and only become active every few seconds to detect and report RSSI data. The device 2 may also be configured to only report RSSI data from base stations 12 when that RSSI value is above a predetermined threshold.

In some embodiments, the device 2 may further include a temperature sensor 38, motion sensor 39, and/or other sensors such as an accelerometer. Measurements from one or more of these sensors may be included in data reported to the central computer 20. Additionally, the motion sensor 39 may be used to regulate the frequency with which the device 2 reports RSSI data to the central computer 20: for example, the device 2 may report data every three seconds by default, but more frequently when the motion detector indicates to processor 34 that the device 2 is in motion or is in a high risk area of the environment. Parameters governing the motion sensor 39, such as a measurement threshold indicating that the device 2 is in motion, may be set dynamically based on instructions sent from the central computer 20. The central computer 20 may monitor motion and/or temperature data and use this as the basis for various reports 46 and/or alerts 44 issued to users and administrators. Furthermore, in some embodiments, the base stations 12 also have temperature sensors 38 and include temperature data in their reports to the central computer 20, e.g. temperature data may be measured and reported upon detecting activation of a hand hygiene station usage sensor 16.

Under certain conditions, such as a determination that a user is not in compliance with the hand hygiene protocol, the central computer 20 may generate or issue an alert 44 to notify the user and/or other persons. These alerts 44 may be used to notify the user via messages sent to the device 2, to another person via a similar device 2, or to the user or another person via an alternative alert system. Such alternative alert systems may comprise warning lights or loudspeakers activated via a third party notification system, SIP/VoIP interfaces to phone systems, email (SMTP), SMS messages, SNPP and WCTP messages to pagers, SNMP alerts over a network, external input/output to appliances connected to the computer 20, or other means of alerting someone in the environment. Alerts issued by central computer 20 may be used to notify a device user, a worker, an administrator, or a patient or customer of non-compliance or other relevant events, such as an extreme temperature condition or a hand hygiene station 24 that needs its fluid reservoir 29 refilled. If an alert is issued and sent to the device 2, the device 2 may notify the user via an audible alert notification such as a ringtone or beep, a visual alert notification such as a flashing light or indication on the device 2 screen, a vibratory alert notification, or any other method of bringing the alert event to the user's attention. In addition to reporting non-compliance, alerts 44 may be issued by the central computer 20 indicating compliance with the hand hygiene policy 42.

In addition to various alerts 44, the central computer 20 may generate or issue more detailed reports 46 based on the data it receives from devices 2 and base stations 12 in the environment. The computer 20 may issue reports 46 for sending to individual users or to administrators showing rates of hand hygiene compliance, either by the recipient user or by one or more other users. For example, reports 46 may be issued showing unusual or noteworthy behavior or conditions, such as extreme temperature readings, unusual patterns of motion reported by devices 2, high rates of non-compliance with the hand hygiene policy 42, or reported use of hand hygiene stations 24 by persons not reporting to the system 1. Reports 46 may be issued on equipment maintenance needs, such as reports showing low battery levels in batteries 37 on devices 2 or base stations 12, reports identifying hand hygiene stations 24 needing fluid 28 refills, reports showing power change states for base stations 12 indicating that a station has lost its primary power source and is using its secondary power source, or reports showing that a device 2 or base station 12 has stopped reporting to the computer 20, to other devices 2, and/or to other stations. Patterns of data from different sources may be combined to compose the content of a report 46 or to trigger its generation.

For instance, in example embodiments a hand hygiene station 24 reporting activation of its usage sensor 16 without a corresponding proximity report from a nearby device 2 may trigger any one of three reports 46 depending on other factors: it may trigger a report about a visitor using the station, a report about the station having been moved (if the system 1 also detects changes in the station's radio environment as reported by one of the devices 2), or a report about a user's device 2 having a dead battery 37 (if one or more devices 2 reported a low battery 37 level prior to the use of the station). Reports 46 may summarize data over a set period of time, such as a daily, weekly, or monthly report; they may also be segmented by a region of the environment (e.g., a specific ward of a hospital), by a class of user or device, or by other criteria.

These reports 46 may be sent to a device 2, where they may be accessed by a user through the device's user interface 11. The reports 46 may also be sent to a user or administrator's device or computer via various communication systems available to the computer 20 as outlined above (e.g., SIP, email, SMS), or accessed directly by an administrator present at the computer 20 through a screen or other user interface 11. Additionally, any of these reports 46 may also be sent to some users in the form of simpler alerts 44 as described above. In one embodiment, different alerts 44 are issued and sent to users upon performing compliant and non-compliant hand hygiene events, and an email summary of each user's policy compliance is issued and sent at the end of each shift, allowing users to review their performance and dispute or explain any missed compliance events. The rules used to determine what events in the system 1 lead to what kinds of alerts 44 and reports 46, sent to whom, may be set by an administrator of the system 1 at the central computer 20. For example, such rules may be part of the hand hygiene policy 42 that is stored on database 49 that is accessible to the central computer 20.

Some reports 46 may contain text partially populated by database fields. For example, a daily compliance report 46 for a ward of a hospital may comprise boilerplate text with certain variable fields (the name of the ward, the date, the rates of compliance and non-compliance, the number of users in that ward, etc) populated by field information from the database 49 based on preset values and dynamic collected data. Some or other reports 46 may be represented visually as maps or floor plans of the environment with icons displaying points of interest, e.g. with underused stations or stations in need of maintenance marked on the map as red icons, and normal operating stations marked as green icons.

In addition to or as part of reports 46 and alerts 44, an administrator or user accessing the central computer 20 through, e.g., a terminal or web interface may perform specific data queries to track information about the system 1. An administrator might track the location of a user in the system 1, either at a specific time or over a period of time, based on the reported radio environment of that user's device 2. An administrator might also monitor the system 1 to locate rogue wireless access points detected by devices 2 but not part of the network infrastructure of the system 1; these rogue access points could be located based on their reported RSSI and scheduled for investigation by administrators. An administrator might monitor areas or time periods corresponding to known infection outbreaks and examine the compliance data associated, with those areas or periods in order to devise remedial procedures. An administrator might monitor over and under-utilization patterns of hand hygiene stations 24 in order to decide whether one or more stations should be added to, moved within, or removed from the system 1. Individual devices 2 or stations can be located within the system 1, and compliance or non-compliance events can be viewed in real time. Using a combination of alerts 44, reports 46, and real-time interactive data queries, administrators can monitor and respond to changes and events in the environment, and they can formulate new policies or predict the effects of proposed policies on the existing environment.

In one embodiment, different devices 2 and base stations 12 are represented at the central computer 20 by database records linked to a unique identifier. A device 2 or station 12 may be categorized into one or more groups based on its characteristics stored in the database 49: for example, a specific hand hygiene station 24 (identified by its MAC address) may at one time belong to one or more of the groups "hand wash stations", "stations in a patient environment", "stations on the $3^{rd}$ floor", "stations in room 312", "stations mounted on a patient bed", "stations in need of hand washing fluid refill", "stations currently unplugged from wall power", and "station with low battery power". These group memberships can be used to generate reports 46, and certain users or administrators may have access to information pertaining only to certain groups of devices 2 or stations 12. These groups may also be used by the central computer 20 to set default parameters for the station used in determining compliance, such as the RSSI readings corresponding to proximity thresholds used in determining compliance. Membership of a device 2 or station in these various groups may change dynamically based on information gathered by the central computer 20.

The device 2 in some embodiments has a power source 37, such as a battery, for powering its operations. The device 2 may report the remaining power level of its power source to the central computer 20, and the central computer 20 may use this data as the basis for alerts 44 or reports 46 sent to the device 2 or elsewhere. The device's 2 power source 37 may be rechargeable by means of, e.g., a mini universal serial bus (USB) port. The base stations 12 in some embodiments also have a power source 37, which may comprise a battery, direct power, power over Ethernet, or solar panels. Reports from a base station 12 to the central computer 20 may also include power level data.

The interaction of the different parts of the system 1 according to example embodiments is shown in FIG. 1. The device 2 includes a memory 36 storing instructions for the processor 34 to implement a proximity detection module 6, communication module 8, and user interface module 10. The proximity detection module 6 receives RSSI readings from the wireless access points 26, infection risk stations 22, and hand hygiene stations 24 using the radio transceiver 4. The communication module 8 communicates with the central computer 20 via the radio transceiver 14 in wireless communication with the wireless access points 26. The device 2 also includes a power source 37, a temperature sensor 38, and a motion sensor 39, each of which reports its state to the central computer 20 via the communication module 8. Each base station 22, 24, and 26 has a radio transmitter 14 broadcasting as a wireless access point, allowing the device 2 to read its RSSI. In some example embodiments, infection risk stations 22 and hand hygiene stations 24 can be implemented as fully functional wireless LAN wireless access points with wired connectivity to network 40, however in some embodiments infection risk stations 22 and hand hygiene stations 24 can be implemented using a wireless communications devices having a configuration similar to that of mobile device 2, and could for example be implemented using an active RFID tag including for example a 802.11a/b/g or n enabled tag, and in some cases infection risk stations 22 and hand hygiene stations 24 may be implemented using devices that simply transmit an identifier.

As noted above, in some example embodiments, the hand hygiene station 24 has a fluid dispenser 27, fluid reservoir 29 and a usage sensor 16, and it uses its radio transmitter 14 to send usage data to the central computer 20 via the wireless access points 26. The central computer 20 receives data from the devices 2 and the hand hygiene stations 24 via the wireless access points 26, with which it communicates through the network 40. The central computer stores the received data in the database 49 and generates alerts 44 and reports 46 based on the data. Messages representing alerts 44 and reports 46 can be sent to the device 2 and communicated to the user via the user output by means 30 of the user interface 11 controlled by the user interface module 10. The user can access and control further features of the device 2 through the user input means 32 of the user interface 11.

The specific methods used by the central computer 20 to determine compliance with a hand hygiene policy 42 based on the proximity and hand-washing event data will vary depending on the specific policy 42 in place. The policy 42 may be changed by an administrator through the computer's user interface 21. Different policies or policy rules may be applied to different device 2 types, or to different users, or to different areas of the environment (such as using a more strict policy in an intensive care ward of a hospital or a ward which has a history of infection). Several features of example policies are described below, but the system 1 is not limited to these embodiments.

In one example policy 42, a user may be deemed out of compliance if he or she passes within a predetermined proximity to any hand hygiene station 24 without washing his or her hands. In another example policy 42, a user is deemed out of compliance if he or she passes within a set distance of an infection risk station 22 and stays there for a set period of time without having washed his or her hands within a predetermined amount of time beforehand. In a further policy rule, a user may be deemed out of compliance if he or she comes into proximity with a first infection station for more than a set period of time, then comes into proximity with a second infection risk station 22 without washing his or her hands in between. A user in a hospital environment may be deemed out of compliance if he or she comes into proximity with a hand hygiene station 24 mounted inside a patient room without triggering a compliant hand washing event, unless the same user previously triggered a compliant hand washing event at a hand hygiene station 24 in the hallways adjacent to the patient room. These policies may be altered in various ways: for instance, instead of the infection station itself being the relevant area indicating risk, the relevant area may be an entire patient environment, as indicated by a preset proximity to patient beds as well as other stations mounted within a patient's room. A policy 42 may also combine two or more of these criteria, or may include additional factors ascertainable from the data available to the computer 20.

Figure 2:
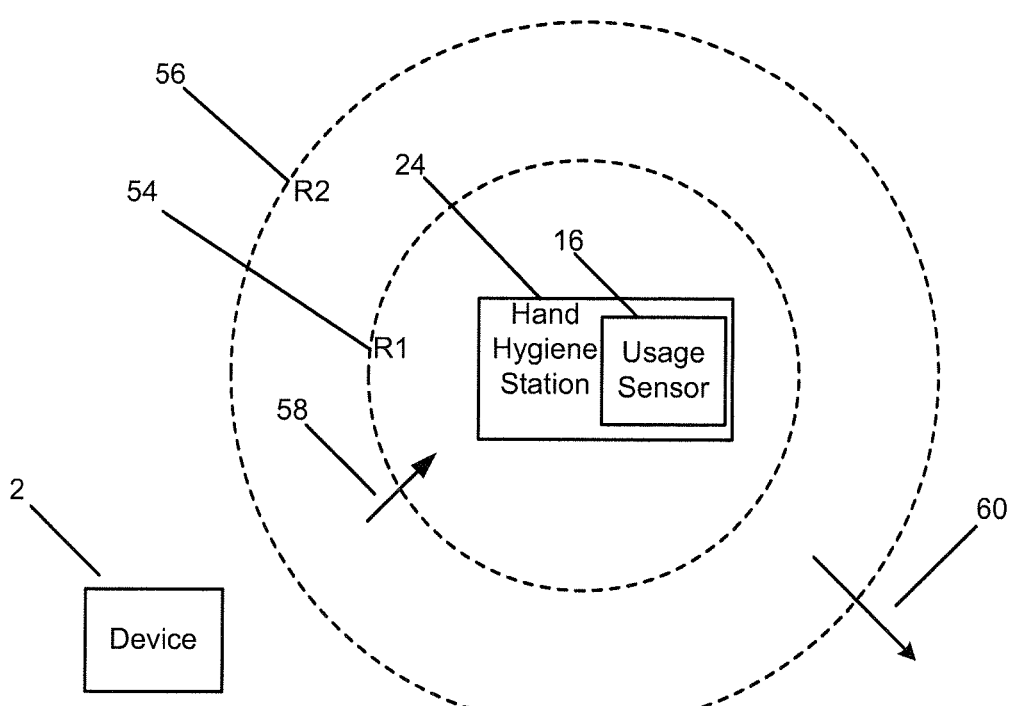
FIG. 2 is an schematic overhead view of a base station illustrating the determination of a device's proximity to the base station.
Figure 3:
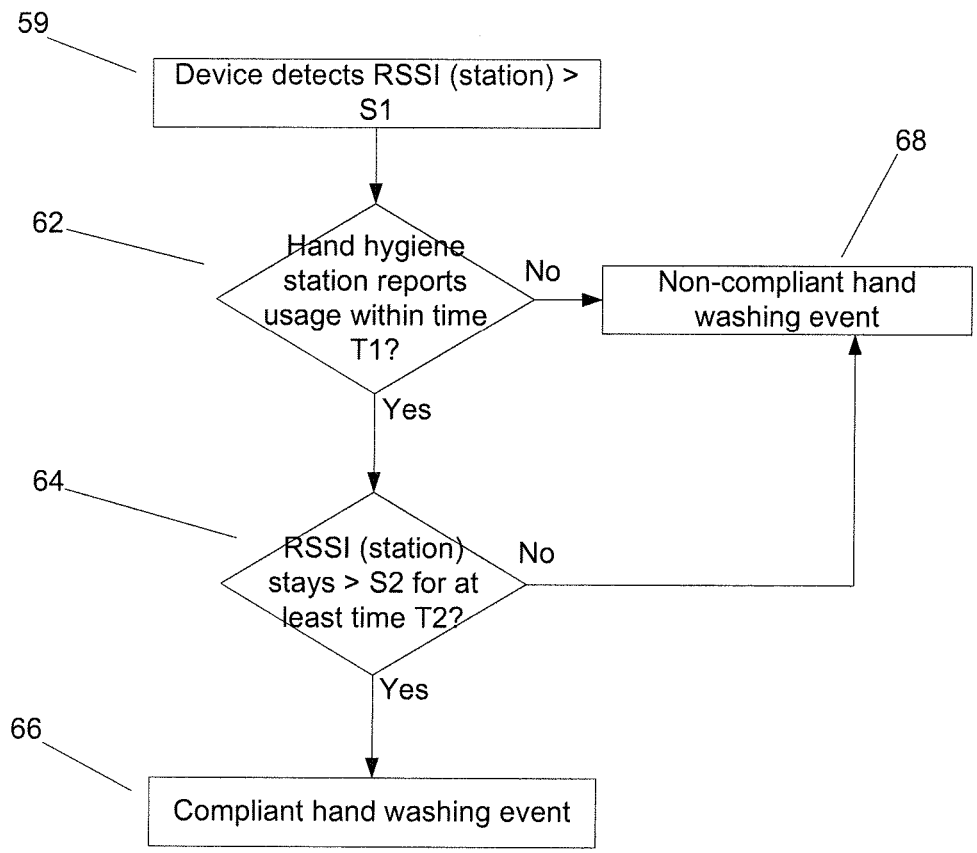
FIG. 3 is a flow chart showing an example method of determining that a user has washed his or her hands.

Determining whether a user has washed his or her hands at a given hand hygiene station 24 can be accomplished by the method shown in FIG. 2 and FIG. 3, according to example embodiments. At step 59 of FIG. 3, the user's mobile device 2 detects an RSSI from a hand hygiene station 24 above RSSI threshold S1, indicating that the user is within radius R1 54 (See FIG. 2) of the station (i.e., a proximity ingress event as illustrated by arrow 58). In particular, as will be apparent from the preceding description, over time the mobile device 2 transmits a series of data messages or records to the central computer 20. Each of the records includes an identifier for the mobile device 2 as well as identification information for stations 22, 24 or 26 that the mobile device can detect at that given time, and RSSI information for such stations. The central computer 20 uses the information included in the data messages that it receives from the mobile device 2 to determine when and if the proximity threshold R1 for a given hand hygiene station 24 has been crossed by comparing the RSSI readings reported by the device 2 against the RSSI proximity threshold S1 for the station 24 stored at the central computer 20. At this point, the user must activate the usage sensor 16 of the station within time T1 62 to remain in compliance. By way of example, the usage sensor 16 may be activated when a fluid dispenser 27 at the hand hygiene station 24 is activated. After the usage sensor 16 has registered use and reported it to the computer 20 (for example via a message sent by hand hygiene station 24 through wireless access point 26) at step 62, the user must remain within radius R2 56 of the station for at least time T2 64 to remain in compliance, indicating that the user is continuing to engage in hand hygiene activity for the requisite period of time. This continuing proximity is measured at the central computer 20 by checking that the station 24 RSSI reported by the device 2 remains above threshold S2—i.e., no proximity egress event as indicated by arrow 60 occurs— during the specified period T2. If all these steps are satisfied, the computer 20 registers or records a compliant hand washing event 66 for the user of the mobile device 2; otherwise, the computer 20 does not register the user as having properly participated in a compliant hand washing event, and may instead record a missed compliance event 68. In one non-limiting example embodiment, radius R1 54 is smaller than radius R2 56 (meaning that S1 is greater than S2), T1 is two seconds, and T2 is three seconds. Recording or registering a compliant or non-complaint hand hygiene event can include writing an event record to database 49 that allows the mobile device 2, the hygiene station 24, and the time of the event to be identified, among other things.

A similar method and similar parameters may be used to determine time in proximity to an infection risk station 22.

This method described in respect of FIGS. 2 and 3 may be altered or varied in several ways while remaining effective. For example, the usage sensor 16 and associated data may be eliminated, based on the presumption that the user is spending time at the station for the purpose of hand washing. The time limits T1 and/or T2 may be ignored, counting the user as compliant as long as the hands are washed after entering R1 54 and before leaving R2 56. The values of parameters S1, S2, R1 54, R2 56, T1, and T2 may be altered or varied depending on the device 2 identity or type, base station 12 identity or type, location, time, previous activity by that device 2, or some other factor ascertainable by the computer 20. In addition, patterns of behavior may be taken into account that indicate that the user has attempted compliance but has been unable to comply: for instance, a user who attempts to use a hand hygiene station 24 with an empty fluid reservoir 29 or a missing fluid cartridge may be counted as compliant if that user proceeds within a set time limit to a second hand hygiene station 24 and executes a valid hand washing procedure there. The rules determining what events constitute compliance or non-compliance, and how the system 1 responds to or reports such compliance and non-compliance, may be set at an administrator at the central computer 20.

The central computer 20 in some embodiments stores reported data and preset data on the environment, including devices 2 and stations, in a database 49. As proximity data, hygiene station 24 usage data, and other data are received by the central computer 20, they are associated with a date and time stamp and stored as records in the database 49. This data may from time to time be optimized or flattened by only retaining calculated events, rather than all raw data, in the database 49. Thus, RSSI measurements from devices 2 may be purged from the database 49 after a set period of time has elapsed, with only the determinations of proximity and other relevant events retained as database entries. This still allows re-examination of this data in the event of a policy change that redefines the way compliance is calculated (for instance, changing the definition of a compliant hand hygiene event to include a 5-second window instead of a 3-second window) while allowing data to be efficiently archived over long periods. The types of events retained may include proximity ingress events, proximity egress events, hand hygiene station 24 usage sensor 16 events, low battery 37 events, extreme temperature events, low fluid 28 level events, fluid 28 refill events, power state change events (i.e. a station becoming unplugged), and button press events. Alternatively, in another embodiment, all data is retained in the database 49, with only duplicate data (such as multiple RSSI reports from a stationary device 2 in a static radio environment) being removed in the flattening process.

The computer 20 may further be configured to monitor additional data about the system 1, such as temperature reports sent in by devices 2 or base stations 12 or indications that a hand hygiene station 24 has exhausted its supply of hand washing fluid 28. The latter may be accomplished by counting the number of times the usage sensor 16 of the station has reported usage since the last time the station's reservoir 29 of fluid 28 was replenished. By estimating the total amount of fluid 28 used since the last refill based on a known average amount dispensed per use, the computer 20 can predict when a station is likely to need to be refilled.

When a hand hygiene station 24 has its fluid reservoir 29 refilled, the refill may be communicated to the computer 20 in one of several ways. The station may have a button or other sensor to signal refilling, which may be activated by a user's finger or a specialized tool used by maintenance staff, or which may automatically read when a reservoir 29 is refilled or a new reservoir cartridge is inserted. Alternatively, the device 2 may have a refill signaling module used by maintenance staff, allowing someone who refills a station to indicate the refill through the user interface module 10 of the device 2, thereby sending this data to the computer 20 via the radio transceiver 4. The central computer 20 may also record who serviced the station based on the device's reported proximity data. In some example embodiments, the fluid reservoir 29 could include a fill level sensor 29A such as a scale or floatball switch for reporting fill level information back to the central monitoring computer 20 through transceiver 14. Based on fill-level information received from the fill level sensor 29A, the central computer could track when a hand hygiene station 24 needs to be refilled and subsequently has its fluid reservoir 29 refilled, and could send out alert or other notification messages as required to ensure the reservoir is kept at a required fluid level.

In one embodiment, the base stations 12 have communication capabilities similar to those of the device 2, e.g. a radio transceiver 4 and a processor 34 running software allowing the station to communicate with the computer 20 and to dynamically reconfigure its operations in response to instructions from the computer 20, including network communication parameters. Some embodiments may actually use the same radio transceiver 4 and associated hardware (e.g. processor 34, memory 36) in the device 2 and the base stations 12 in the form of a standardized radio tag. In addition to reporting usage sensor 16 data, the station may also communicate fluid 28 refill notifications, battery 37 power levels, and other data to the computer 20. In one embodiment, the hand hygiene stations 24 and infection risk stations 22 send out radio beacons in the identifying them as wireless 802.11 access points.

Different embodiments of the device 2 may have different capabilities. Some may not be capable of issuing user alerts 44, or may be capable of issuing alerts 44 but not displaying reports 46. Some devices 2 may be more limited in their ability to configure their RSSI thresholds or network parameters than the embodiments described. However, the system 1 should be able to perform the functions described with several different device types operating on the system 1 at the same time. An indication of the device type may be part of the reports sent to the computer 20 by the device 2, and this may affect how the computer 20 determines whether the user of that device 2 is in compliance. Devices 2 may be carried or worn by users, e.g. by being attached to lanyards or belts.

Alternative embodiments of the system 1 and device 2 may alter one or more of the features described. Some or all of the compliance calculations described as taking place at the computer 20 may instead occur on the devices 2 themselves, and data from the base stations 12 may be relayed to the devices 2 to assist in such calculations. Instead of radio signals, the communication and/or proximity detection features may be accomplished by other means such as infrared or other electromagnetic signals; ultrasonic signals; motion detectors; GPS systems; or any combination of such systems.

In one embodiment of the system 1, the messages sent to the central computer 20 from the devices 2 and the base stations 12 are identical, and the software running on the devices 2 and base stations 12 is identical except for the base stations' feature of broadcasting as an 802.11 access point. In this embodiment, the messages comprise three main sections: a header, a message body and a footer. The header is a fixed length, while the message body is a variable length section. The footer contains a cyclic redundancy check (CRC) to ensure data integrity. The message length can be calculated based on the parameters found in the header. The header includes the station or device ID, the temperature, the battery 37 state, the usage sensor 16 state or device user input state (e.g. whether a button is being pressed on the device 2), the device 2 or base station 12 firmware or software version, and the number of records to follow in the message body. The message body contains a record for each access point 26, infection risk station 22, or hand hygiene station 24 detected in the radio environment. Each record in the message body contains the station 12 or access point 26 identifier (MAC address), and the minimum, maximum and average RSSI (signal strength in dBm, measured over a configurable time period). The message is a UDP datagram which requires low network overhead and no pre-established connection between the device 2 and/or base station 12 and the central computer 20. Both the device 2 and the station 12 report back to the computer 20 using the identical message format. The records are formatted to accommodate transmission over a network using, but not limited to, IPv4 or IPv6 formats for station MAC addresses. The messages may also contain other information, such as a message count field used by the central computer 20 to determine whether a message is a duplicate of an earlier one or if a message from a device 2 or station has been lost. The computer 20 will automatically disregard duplicate messages if the system 1 was able to deliver all the messages successfully. The device 2 is also capable of re-sending a message to the central computer 20 to ensure delivery. This is triggered by a retry counter sent to the device 2 from the computer 20 as part of the network configuration parameters. This is particularly helpful if the system 1 uses a protocol with unverified connections, such as UDP, for messaging.

Accordingly, in example embodiments the system 1 can leverage a facility's wired and wireless infrastructure (including for example, a facility's 802.11a/b/g and/or n Wifi wireless network) to provide real time monitoring and reporting of hand hygiene events. The facility's wired and wireless infrastructure is used to back haul messages from the user's mobile electronic devices 2, hand hygiene stations 24 and infection risk stations 14 to the central compliance computer 20. The system can report both successful and unsuccessful or missed hand hygiene events, with different policies in place for different classes of users and different locations within a facility. Immediate feedback can be provided to users of mobile electronic devices 2 through audible beeps or physical vibrations for example.

According to one example embodiment a mobile electronic device for monitoring hand hygiene policy compliance in a system that includes at least one hand hygiene station at which a user of the mobile electronic device can perform a hand hygiene action, comprising: a radio transceiver; a processor controlling operation of the mobile electronic device and exchanging signals with the radio transceiver, the processor being configured to measure a strength of at least one wireless signal received from at least one hand hygiene station through the radio transceiver; and communicate signal strength information about the wireless signal to the central computer via the radio transceiver and to receive notification of compliance or non-compliance with the hand hygiene policy from the central computer. The device can also include a motion sensor connected to the processor, wherein the processor is further configured to send proximity data to the central computer more frequently when the motion sensor detects that the device is in motion. The processor can also be configured to receive an user input indicating that the hand hygiene station has had its hand hygiene fluid replenished, and to send an indication to the central computer of such hand hygiene fluid replenishment.

In some example embodiments, at least some of the processing being done to determine compliance on non-compliance with hand hygiene policy 42 may be done at mobile devices 2. For example, some of the policy rules and parameters values of parameters S1, S2, R1 54, R2 56, T1, and T2 for various hand hygiene stations could be uploaded to mobile devices 2, and the devices 2 could then determine compliant events and non-complaint events using their own processing systems and send alert messages and reports back to the central computer 20.

The embodiments described herein are examples of structures, systems or methods having elements corresponding to the elements of the invention recited in the claims. This written description may enable those skilled in the art to make and use embodiments having alternative elements that likewise correspond to the elements of the invention recited in the claims. The intended scope of the invention thus includes other structures, systems or methods that do not differ from the literal language of the claims, and further includes other structures, systems or methods with insubstantial differences from the literal language of the claims.

The invention claimed is:

1. A method for monitoring hand hygiene policy in a communication system that includes at least one mobile electronic device having a radio transceiver, at least one wireless base station and a central computer, comprising:
   detecting through the radio transceiver of the mobile electronic device at least one signal of at least one radio transmitter of at least one base station;
   communicating signal strength data indicating the strength of at least one signal from the mobile electronic device to the central computer by means of the radio transceiver; and
   determining at the central computer whether a user of the mobile electronic device is in compliance with a hand hygiene policy based at least partially on the signal strength data received from the mobile electronic device;
   wherein the at least one base station comprises a hand hygiene station at which the user can perform a hand hygiene event, the hand hygiene station comprising a usage sensor adapted to detect a hand hygiene event at the hand hygiene station, the method further comprising the steps of: sensing a hand hygiene event at the hand hygiene station by means of the usage sensor; and communicating data indicating the sensed hand hygiene event from the hand hygiene station to the central computer by means of a radio transmitter of the hand hygiene station;
   wherein determining at the central computer whether the user is in compliance with the hand hygiene policy is also based on the hand hygiene event data from the hand hygiene station; and
   wherein the step of determining whether the user is in compliance comprises determining whether the user has cleaned his or her hands by: determining, in dependence on the signal strength data, that the user was within a first predetermined proximity to the hand hygiene station when the hand hygiene event occurred; and determining, in dependence on the signal strength data, that the user remained within a second predetermined proximity to the hand hygiene station for a predetermined length of time after the hand hygiene event occurred;
   wherein the communications system includes at least one infection risk station that includes a radio transmitter and indicates a location where individuals have a higher risk of receiving or transmitting infection, the method further comprising: detecting through the radio transceiver of the mobile electronic device a signal sent from the radio transmitter of the infection risk station; and communicating data indicating the strength of the signal from the infection risk station to the central computer by means of the radio transceiver;
   wherein determining whether the user is in compliance comprises determining, based on the data indicating the strength of the signal from the infection risk station, whether the user has cleaned his or her hands within a second predetermined length of time before entering a predetermined proximity of the infection risk station.

2. The method of claim 1, further comprising: detecting by the radio transceiver of the mobile electronic device a signal sent from a radio transmitter of a further infection risk station; communicating data indicating the strength of the signal from the further infection risk station to the central computer by means of the radio transceiver; and the step of determining whether the user is in compliance further comprises: determining, based on the data indicating the strengths of the signals from the infection risk stations, that the user has washed his or her hands after coming into proximity with the infection risk station and before coming into proximity of the further infection risk station.

3. The method of claim 1, wherein the hand hygiene station dispenses hand hygiene fluid, further comprising the steps of: determining at the central computer whether a hand hygiene station has exhausted its supply of hand hygiene fluid by counting the number of hand hygiene events reported by the hand hygiene station since the fluid was last replenished; and wherein determining at the central computer whether the user is in compliance with the hand hygiene policy is based on the signal strength data received from the mobile electronic device, the hand hygiene event data from the hand hygiene station, and the determination as to whether the hand hygiene fluid has been exhausted.

4. The method of claim 1 further comprising sending an alert message from the central computer to the mobile electronic device if the user is determined to be out of compliance with the hand hygiene policy.

* * * * *